United States Patent
Sukumaran et al.

(10) Patent No.: US 10,781,220 B2
(45) Date of Patent: Sep. 22, 2020

(54) PYRENE TETRA BORONIC ACID, PROCESS FOR PREPARATION AND USE THEREOF

(71) Applicant: COUNCIL OF SCIENTIFIC AND INDUSTRIAL RESEARCH, New Delhi (IN)

(72) Inventors: Santhosh Babu Sukumaran, Pune (IN); Vivek Chandrakant Wakchaure, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/610,020

(22) PCT Filed: Apr. 27, 2018

(86) PCT No.: PCT/IN2018/050261
§ 371 (c)(1),
(2) Date: Oct. 31, 2019

(87) PCT Pub. No.: WO2018/203345
PCT Pub. Date: Nov. 8, 2018

(65) Prior Publication Data
US 2020/0079798 A1 Mar. 12, 2020

(30) Foreign Application Priority Data
May 2, 2017 (IN) .............................. 201711015472

(51) Int. Cl.
*C07F 5/02* (2006.01)
*C09D 11/17* (2014.01)
*G01N 33/58* (2006.01)
*G01N 33/66* (2006.01)

(52) U.S. Cl.
CPC .............. *C07F 5/025* (2013.01); *C09D 11/17* (2013.01); *G01N 33/582* (2013.01); *G01N 33/66* (2013.01)

(58) Field of Classification Search
None
See application file for complete search history.

(56) References Cited

PUBLICATIONS

Yu et al., "Glucose sensing via polyanion formation and induced pyrene excimer emission", Chem Commun., 2009, pp. 1347-1349.
Liu et al., "Specific detection of d-Glucose by a tetraphenylethene-based fluorescent sensor", Journal of the American Chemical Society, 2011, 133, 4, pp. 660-663.
Lerner et al., "Scalable, non-invasive glucose sensor based on boronic acid functionalized carbon nanotube transistors", Appl. Phys. Lett., 2013, 102, pp. 1-4.
Gamsey et al. "The effect of boronic acid-positioning in an optical glucose-sensing ensemble", Tetrahedron, 2006, 62, 2006, pp. 6321-6331.
Kawanishi et al., "A study of boronic acid based fluorescent glucose sensors", J Fluoresc., 2004, 14, 5, pp. 499-512.

*Primary Examiner* — Po-Chih Chen
(74) *Attorney, Agent, or Firm* — Blank Rome LLP

(57) ABSTRACT

The present invention discloses a pyrene tetra boronic acid compound of formula (I) which is useful for permanent writing using water as an ink, glucose sensing and fluorescent labelling application The present application also discloses a process for preparation of said compound.

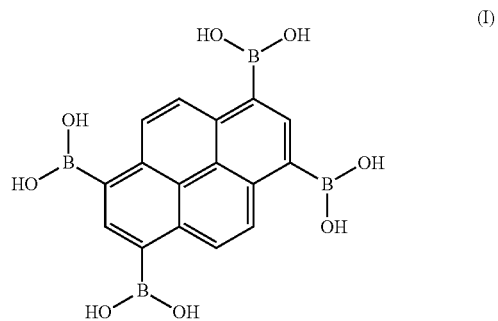

9 Claims, 6 Drawing Sheets

PYRENE TETRA BORONIC ACID, PROCESS FOR PREPARATION AND USE THEREOF

RELATED APPLICATIONS

This application is a national phase application of PCT/IN2018/050261, filed Apr. 27, 2018, which claims priority to Indian Application No. 201711015472, filed May 2, 2017.

FIELD OF THE INVENTION

The present invention relates to a pyrene tetra boronic acid compound of formula I and a process for preparation thereof. The present invention further relates to use of the pyrene tetra boronic acid compound of formula I in irreversible writing using water as an ink, glucose sensing and fluorescent labelling application.

BACKGROUND AND PRIOR ART OF THE INVENTION

The reversible boronic acid-diol interaction empowers boronic acid receptors saccharide binding capacities, rendering them a class of lectin mimetic, termed "boronlectins". Boronic acids follow lectin functions not just in being able to bind saccharides, but in multivalent saccharide binding that enhances both affinity and selectivity. For almost a decade, efforts have been made to achieve and improve selectivity for given saccharide targets, most notably glucose, by using properly positioned boronic acids, offering multivalent interactions. Incorporation of several boronic acid groups into a covalent framework or non-covalent assembly of boronic acid are two general methods used to create such smart sensors, of which the latter resembles lectin oligomerisation that affords multivalent saccharide-binding architectures.

Boronic acids are increasingly utilized in diverse areas of research. Including the interactions of boronic acids with diols and strong Lewis bases as fluoride or cyanide anions, which leads to their utility in various sensing applications. The sensing applications can be homogeneous assays or heterogeneous detection. Detection can be at the interface of the sensing material or within the bulk sample. Furthermore, the key interaction of boronic acids with diols allows utilization in various areas ranging from biological labelling, protein manipulation and modification, separation and the development of therapeutics.

Boronic acids are ideal molecular receptors for 1,2- or 1,3-diols (e.g. monosaccharides) because boronic acid derivatives rapidly and reversibly interact with carbohydrates in aqueous media, and thus importantly the method does not consume the analyte.

Article titled "Glucose sensing via polyanion formation and induced pyrene excimer emission" by C Yu et al. published in Chem. Commun., 2009, 1347-1349 reports glucose binding to boronic acid functional groups attached to a synthetic polymer in an aqueous solution effectively turns the polymer into a polyanion, which induces the aggregation of the positively charged trimethylpentylammonium pyrene derivative, leading to a strong excimer emission and the development of a ratiometric fluorescence glucose probe. The pyrene derivative, trimethylpentylammonium pyrene, containing one positive charge was synthesized according to a literature method. Addition of glucose to an aqueous buffer solution (30 mM Tris-HCl, 30 mM NaCl, pH 9.0) of the boronic acid-containing polymer and the pyrene derivative causes significant emission spectral changes.

Article titled "Specific detection of d-Glucose by a tetraphenylethene-based fluorescent sensor" by Yi Liu et al. published in Journal of the American Chemical Society, 2011, 133 (4), pp 660-663 reports a conceptually new "light-up" biosensor with a high specificity for d-glucose (Glu) in aqueous media. The emission from a tetraphenylethene (TPE)-cored diboronic acid was greatly boosted when the fluorogen was oligomerized with Glu because of restriction of the intramolecular rotations of the aryl rotors of TPE by formation of the oligomer. Little change in the light emission was observed when a tetraphenylethene (TPE)-cored diboronic acid was mixed with d-fructose, d-galactose, or d-mannose, as these saccharides are unable to oligomerize with the fluorogen.

Article titled "Scalable, non-invasive glucose sensor based on boronic acid functionalized carbon nanotube transistors" by MB Lerner et al. published in Appl. Phys. Lett.; 2013, 102, 183113 reports a scalable, label-free all-electronic sensor for D-glucose based on a carbon nanotube transistor functionalized with pyrene-1-boronic acid. This sensor responds to glucose in the range 1 μM-100 mM, which includes typical glucose concentrations in human blood and saliva. Control experiments establish that functionalization with the boronic acid provides high sensitivity and selectivity for glucose. The devices show better sensitivity than commercial blood glucose meters and could represent a general strategy to bloodless glucose monitoring by detecting low concentrations of glucose in saliva.

Article titled "The effect of boronic acid-positioning in an optical glucose-sensing ensemble" by S Gamsey et al. published in Tetrahedron; 2006, 62 (26), pp 6321-6331 reports the quenching of the anionic dye 8-hydroxypyrene-1,3,6-trisulfonic acid trisodium salt (pyranine) with three different boronic acid-substituted benzyl viologens and further reports the fluorescence signal modulation obtained upon addition of glucose to the dye/quencher system Article titled "A study of boronic acid based fluorescent glucose sensors" by T Kawanishi et al. published in J Fluoresc.; 2004; 14(5); pp 499-512 reports boronic acid based anthracene dyes designed, synthesized, and immobilized to solid phase, creating a continuous glucose sensor. Glucose sensitivities of dyes can decrease drastically after immobilization, therefore how to immobilize a dye to solid phase without changing the dye property is a key issue in developing the sensor. The glucose sensitivity of the simplest 1st generation sensor, which is based on an immobilized mono-phenylboronate/single-arm type, came short of the sensitivity requirement for practical use, because of the very moderate fluorescence intensity change over the physiological glucose range.

There is need to develop a new series of boronic acid derivative which shows enhancement in emission and Low concentration glucose sensing for a practical application.

OBJECTIVES OF THE INVENTION

The main objective of the present invention is to provide a pyrene tetra boronic acid compound of formula I.

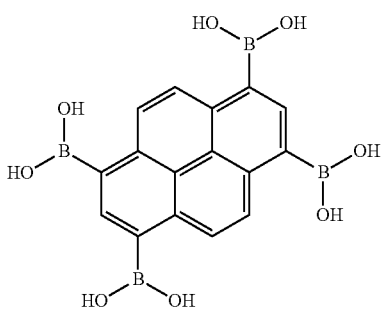

Formula (I)

Another objective of the present invention is to provide a process for the preparation of a pyrene tetra boronic acid compound of formula I.

Still another objective of the present invention is to provide use of the pyrene tetra boronic acid compound of formula I in irreversible writing using water as an ink, glucose sensing and fluorescent labelling application.

SUMMARY OF THE INVENTION

Accordingly, the present invention provides a pyrene tetra boronic acid compound of formula I;

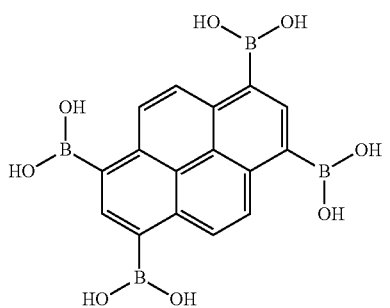

Formula I

In preferred embodiment, the compound of formula I is Pyrene-1,3,6,8-tetrayltetraboronic acid.

In an embodiment, the present invention provides a process for preparation of a pyrene tetra boronic acid compound of formula I comprising the steps of:
 a) adding an alkali metal periodate to a solution of a pyrene derivative in a solvent and stirring the solution for a time period ranging from 24 to 30 hours at a temperature ranging from 25° to 30° C. to obtain a reaction mixture;
 b) adding an acid into the reaction mixture of step (a) at a temperature ranging from 25° to 30° C. and stirring for a time period ranging from 24 to 30 hours to obtain pyrene tetra boronic acid of formula I.

In a preferred embodiment, the pyrene derivative is (1,3,6,8-tetrakis(4,4,5,5-tetramethyl-1,3,2-dioxaborolan-2-yl)pyrene).

In a preferred embodiment, the alkali metal periodates is sodium periodate.

In a preferred embodiment, the acid is hydrochloric acid.

In a preferred embodiment, the solvent is selected from the group consisting of tetrahydrofuran, and water or mixture thereof.

In another embodiment, the present invention provides use of the pyrene tetra boronic acid of formula I in irreversible writing using water as an ink, glucose sensing and fluorescent labelling application.

In still another embodiment, the present invention provides a process for detection of glucose using pyrene tetra boronic acid compound of formula I.

DETAILED DESCRIPTION OF THE INVENTION

The invention will now be described in detail in connection with certain preferred and optional embodiments, so that various aspects thereof may be more fully understood and appreciated.

In an embodiment, the present invention provides a pyrene tetra boronic acid compound of formula I;

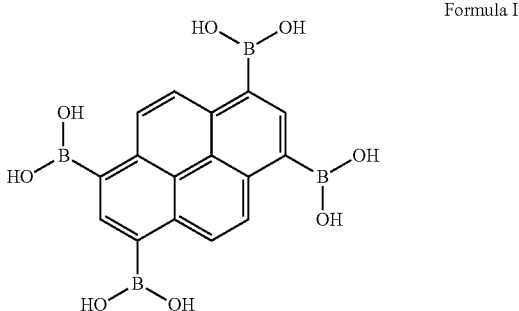 [SMILES: OB(O)c1cc(B(O)O)c2ccc3c(B(O)O)cc(B(O)O)c4ccc1c2c43]

Formula I

The pyrene tetra boronic acid compound of formula I is Pyrene-1,3,6,8-tetrayltetraboronic acid. The pyrene tetra boronic acid compound of formula I show an enhancement in emission with water.

In another embodiment, the present invention provides a process for preparation of a pyrene tetra boronic acid compound of formula I comprising the steps of:
 a) adding an alkali metal periodate to a solution of pyrene derivative in a solvent and stirring the solution for a time period ranging from 24 to 30 hours at a temperature ranging from 25° to 30° C. to obtain a reaction mixture;
 b) adding an acid into the reaction mixture of step (a) at a temperature ranging from 25° to 30° C. and stirring for a time period ranging from 24 to 30 hours to obtain pyrene tetra boronic acid compound of formula I.

The pyrene derivative is (1,3,6,8-tetrakis(4,4,5,5-tetramethyl-1,3,2-dioxaborolan-2-yl)pyrene). The alkali metal periodates is sodium periodate. The acid is hydrochloric acid. The solvent is selected from the group consisting of tetrahydrofuran, and water, or mixture thereof.

The process for the preparation of a pyrene tetra boronic acid compound of formula I as shown in Scheme 1:

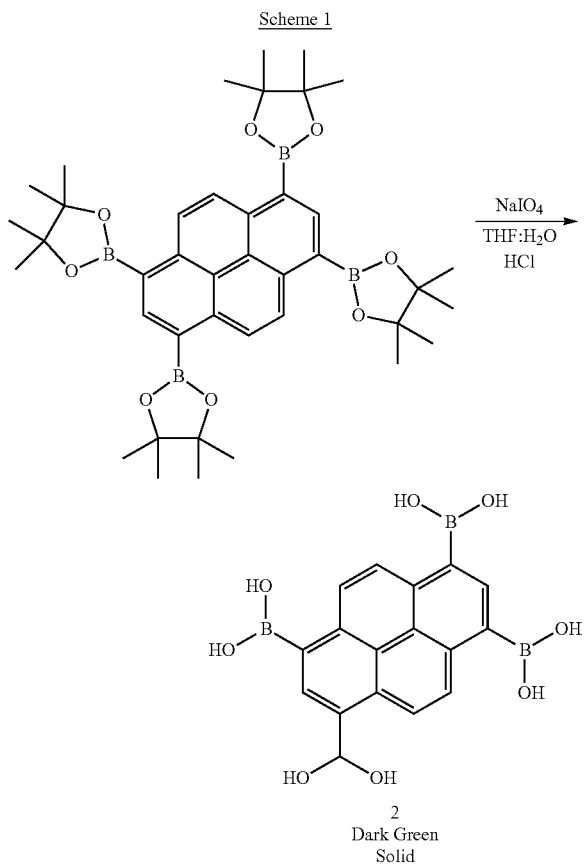

Scheme 1

2
Dark Green
Solid

In still another embodiment, the present invention provides use of said pyrene tetra boronic acid compound of formula I in irreversible writing using water as ink, glucose sensing and fluorescent labelling application.

In preferred embodiment, water is used as ink on pyrene tetra boronic acid as a matrix.

Figure 4:
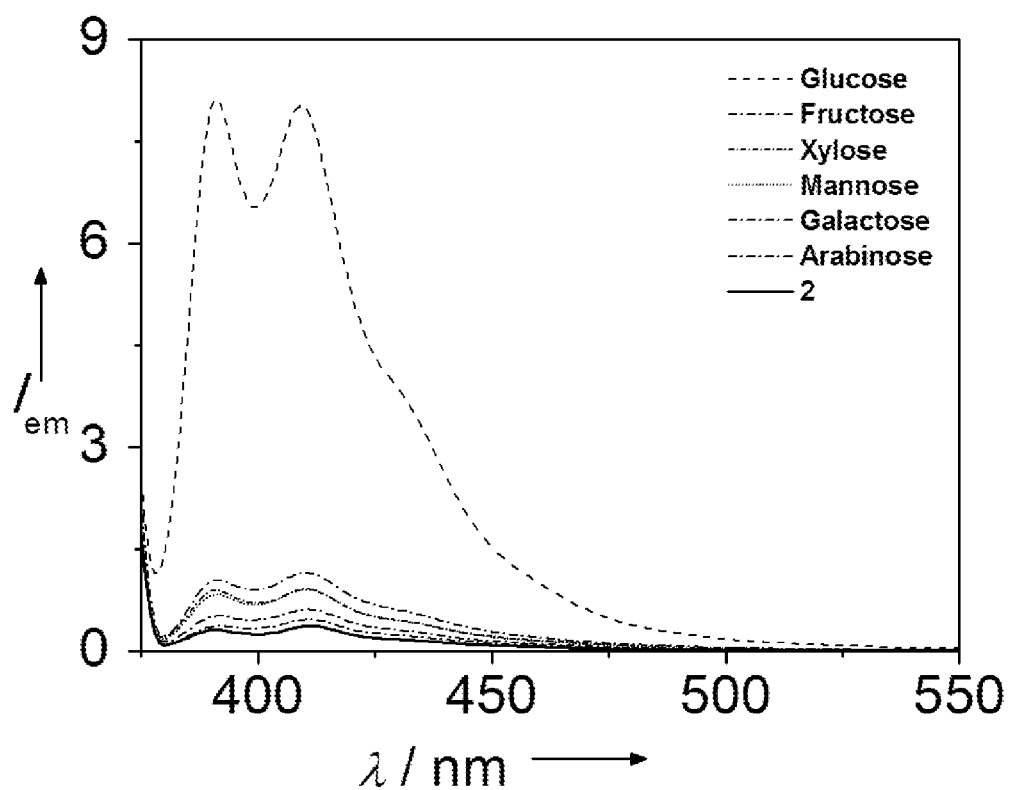
FIG. 4: Emission spectral changes of compound of formula I in EtOAc (C=1×10$^{-7}$ M, 1=1 mm, $\lambda_{ex}$=365 nm) with 1×10$^{-7}$ M solution of various sugars in MeOH (0.7:0.3 ratio).

In an embodiment, the present invention provides a new biosensor with a high specificity for D-glucose in an aqueous media by using the pyrene tetra boronic acid compound of formula I as shown in FIG. 4.

In another embodiment, the present invention provides a pyrene tetra boronic acid compound of formula I which forms sheet-like assemblies and exhibit poor fluorescence and phosphorescence.

In still another embodiment, the present invention provides dip-coated papers made out of paper coated with pyrene tetra boronic acid compound of formula I to enable security labelling via irreversible writing using water as ink.

The present invention provides a process for detection of glucose using pyrene tetra boronic acid compound of formula I, the process comprising titrating a glucose solution with a known concentration of pyrene tetra boronic acid compound of formula I. The titration of equal concentration of monosaccharide's viz, glucose, fructose, xylose, mannose and galactose is carried out. From all of these sugars selective glucose sensing (eight fold enhancements in emission) is observed.

The 2D-sheets formed of the pyrene tetra boronic acid compound of formula I is hydrolyzed and forms hydrogen bonds with water and remain as a permanent fluorescent marking with an enhanced emission.

In still yet another embodiment, the present invention provides a pyrene tetra boronic acid compound of formula I which is used to detect saccharides. It has been surprisingly found that said compound selectively detect D-Glucose while other sugars such as xylose, mannose and galactose exhibit very weak binding. Hence, glucose solution can also be used as an ink for permanent fluorescent marker application using the boronic pyrene tetra boronic acid compound of formula I.

Figure 1:
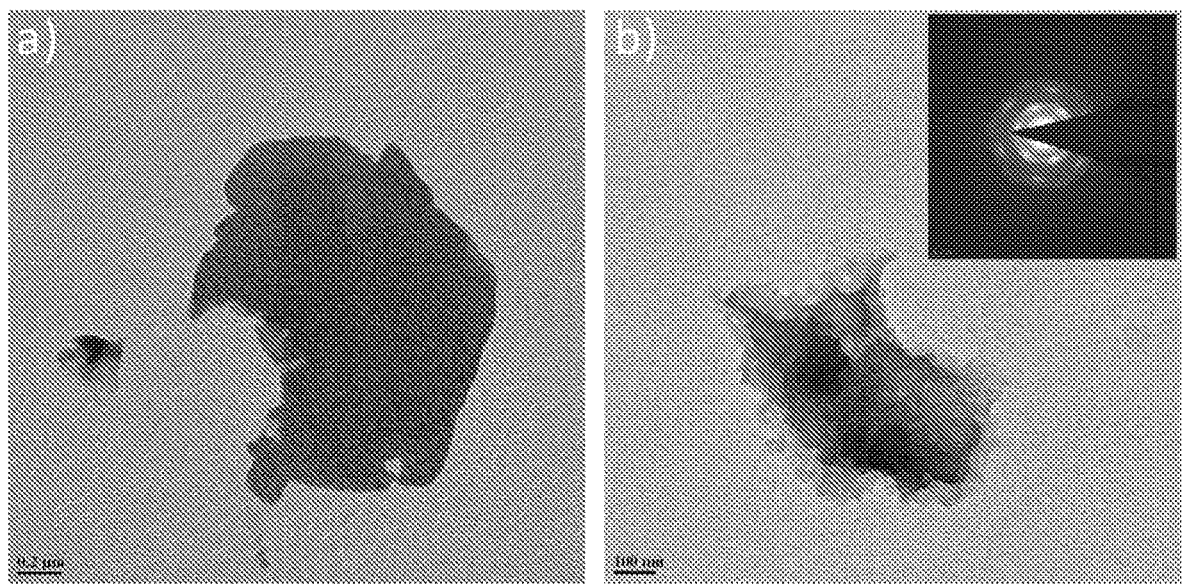
FIG. 1: TEM image of the nanosheet assembly formed by compound of formula I. Inset of b) shows the SAED pattern of the sheets.

FIG. 1 depicts Transmission electron microscopy (TEM) image of the nanosheet assembly formed by compound of formula I. Inset of b) shows the SAED pattern of the sheets.

Figure 2:
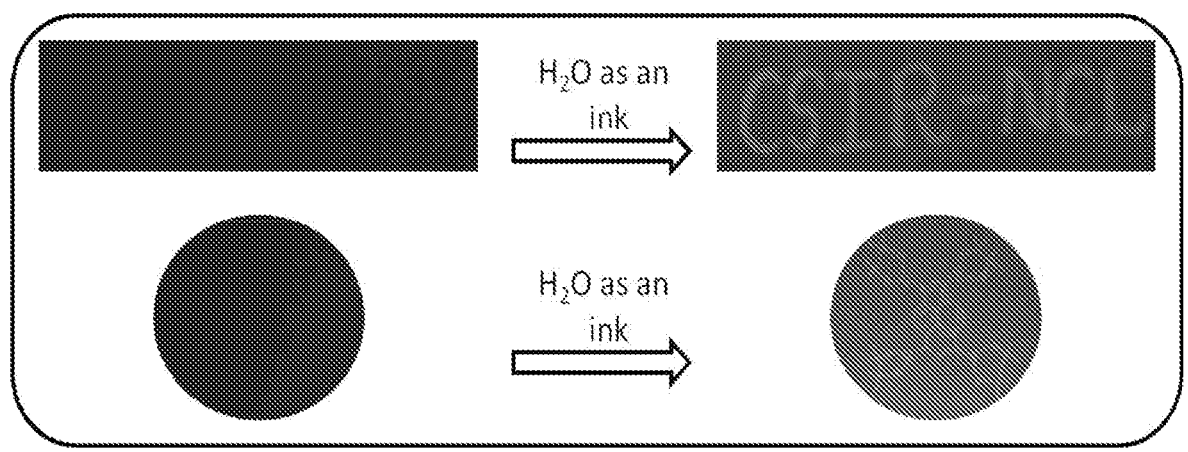
FIG. 2: Irreversible writing on a whatmann filter paper coated with compound of formula I using water as an ink showing enhanced fluorescence.

FIG. 2 depicts irreversible writing on a whatmann filter paper coated with compound of formula I using water as an ink showing enhanced fluorescence.

Figure 3:
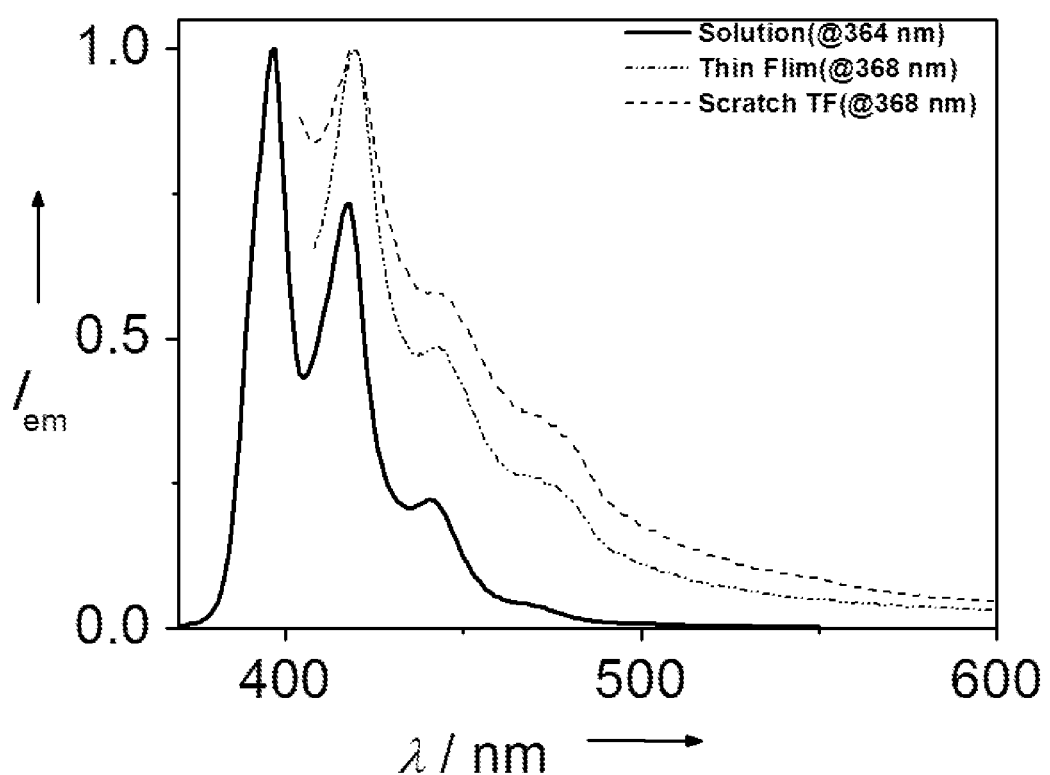
FIG. 3: Normalized emission spectra of compound of formula I in EtOAc solution (C=1×10$^{-3}$ M, 1=1 mm, $\lambda_{ex}$=364 nm), thin film ($\lambda_{ex}$=368 nm) and thin film after scratching for 2 min ($\lambda_{ex}$=368 nm).

FIG. 3 depicts normalized emission spectra of compound of formula (I) in EtOAc solution (C=1×10$^{-3}$ M, l=1 mm, $\lambda_{ex}$=364 nm), thin film ($\lambda_{ex}$=368 nm) and thin film after scratching for 2 min ($\lambda_{ex}$=368 nm).

FIG. 4 depicts emission spectral changes of compound of formula (I) in EtOAc (C=1×10$^{-7}$ M, l=1 mm, $\lambda_{ex}$=365 nm) with 1×10$^{-7}$ M solution of various sugars in MeOH (0.7:0.3 ratio).

Figure 5:
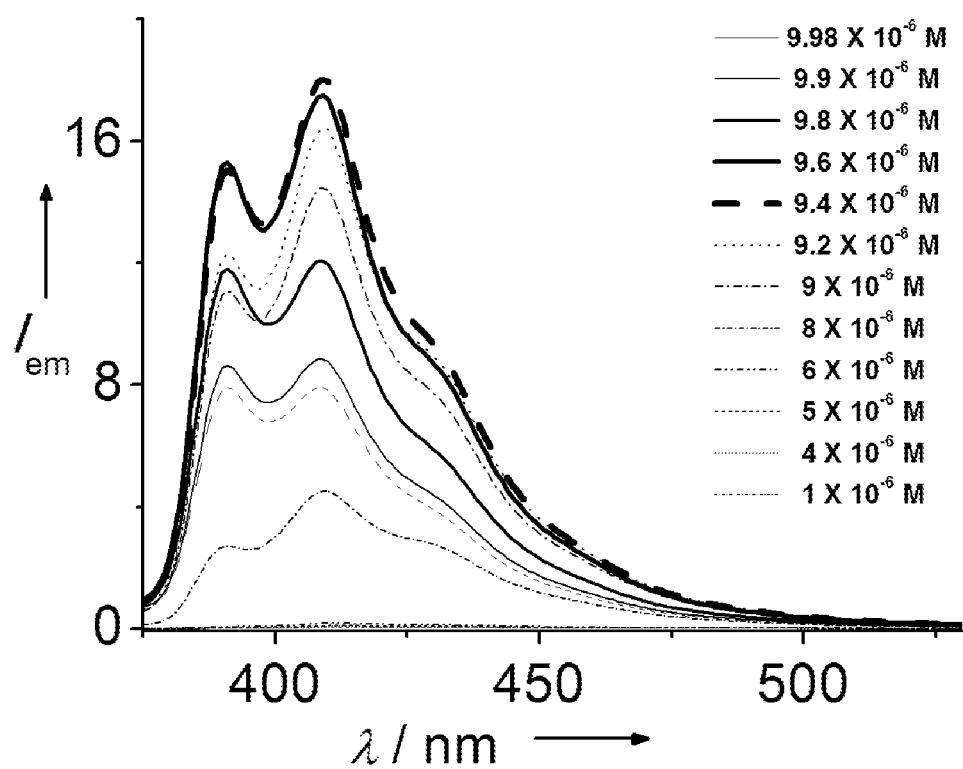
FIG. 5: Emission spectral changes of compound of formula I in EtOAc (C=1×10$^{-3}$ M, 1=1 mm, $\lambda_{ex}$=365 nm) with different molar solution of glucose in MeOH.

FIG. 5 depicts emission spectral changes of compound of formula (I) in EtOAc (C=1×10$^{-3}$ M, l=1 mm, $\lambda_{ex}$=365 nm) with molar solution of glucose in MeOH.

Figure 6:
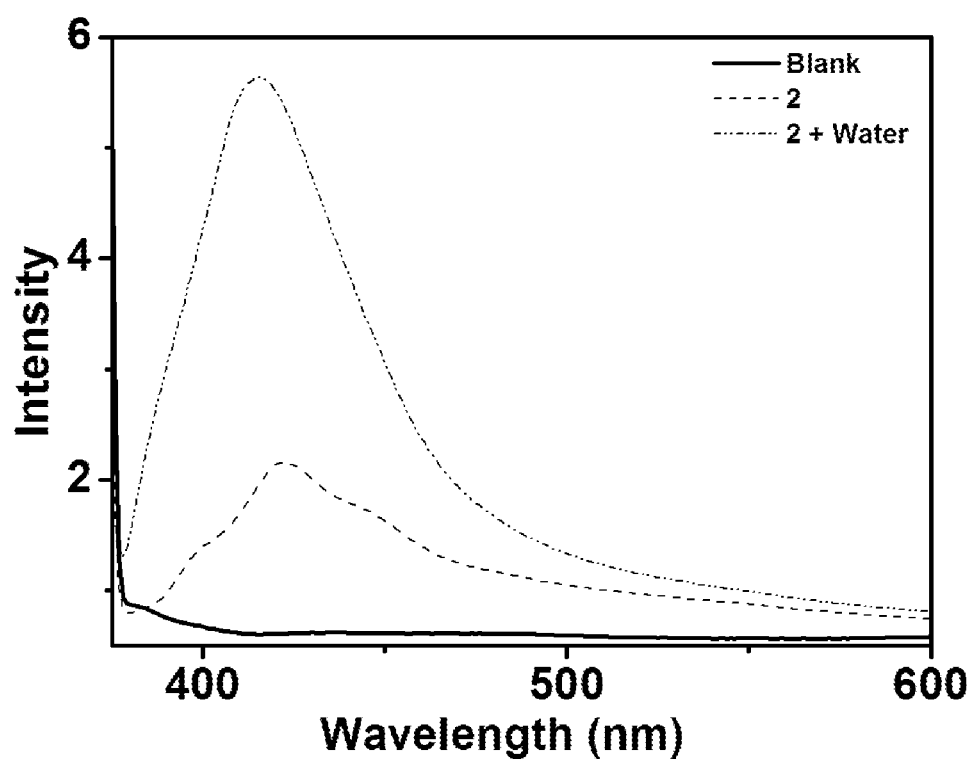
FIG. 6: Emission spectral changes of compound of formula I coated on whatmann filter paper ($\lambda_{ex}$=365 nm).

FIG. 6 depicts emission spectral changes of compound of formula (I) coated on whatmann filter paper ($\lambda_{ex}$=365 nm).

EXAMPLES

Following examples are given by way of illustration therefore should not be construed to limit the scope of the invention.

Example 1: Synthesis of pyrene-1,3,6,8-tetrayltetraboronic Acid

To A solution of (1,3,6,8-tetrakis(4,4,5,5-tetramethyl-1,3,2-dioxaborolan-2-yl)pyrene) (200 mg, 1 eq.) in THF (10 ml) and water (2 ml), sodium periodate (727 mg, 12 eq.) was added. The cloudy suspension was stirred overnight at 25 to 30° C. Then Hydrochloric acid (2M, 0.5 ml) was added and the mixture was stirred for another 24 hours. After the completion of the reaction, the mixture was poured into water, and extracted with ethyl acetate. The organic solvent was removed after drying it with sodium sulphate. The product obtained forms assembly giving a green colour solid. (95%, 101.6 mg) 2D sheet like morphology of the product was confirmed by TEM.

Example 2: Process for the Detection of Glucose

A known concentration of glucose solution was prepared and was titrated with a known concentration of compound formula I. The emission with different molar concentration of sugar was obtained which is provided in FIG. 5. The glucose solution concentration was varied from $9.98 \times 10^{-6}$ M to $1 \times 10^{-6}$ M. It was observed that the emission intensity changed depending upon the glucose concentration. It was further observed that up to $10^{-6}$ M concentration of glucose can be sensed using the compound of formula I.

A. Preparation of a Thin Film on Whatman Filter Paper

Compound of formula I (3.78 mg) was dissolved in 10 ml of ethyl acetate. The resulting solution (C=$1 \times 10^{-3}$ M) was coated on a Whatman filter paper and kept for 25 min at RT for drying. This coated Whatman filter paper emitted a deep blue colour.

B. Permanent Writing Experiments

The Whatman filter paper coated with Compound of formula I was used for permanent writing experiments. A ball pen having a refill filled with water or Glucose solution was taken and written on the Whatman filter paper. It was observed that after writing, the emission of written text enhanced. This enhanced emission was a permanent change on the paper.

ADVANTAGES OF THE INVENTION

1. The pyrene tetra boronic acid compound of formula I compound shows enhancement in emission with water.
2. The pyrene tetra boronic acid compound of formula I show selective glucose sensing (eight fold enhancement in emission) in presence of other saccharides such as xylose, fructose, mannose, galactose and arabinose.

We claim:
1. A pyrene tetra boronic acid compound of formula:

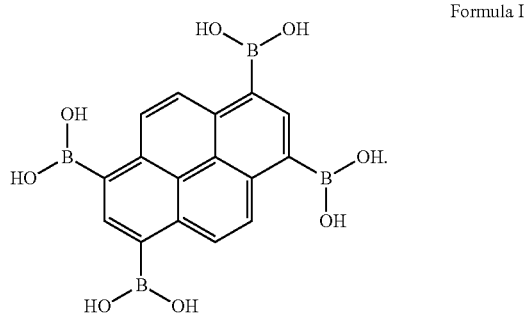 [SMILES: OB(O)c1cc(B(O)O)c2ccc3c(B(O)O)cc(B(O)O)c4ccc1c2c43]

Formula I

2. The compound as claimed in claim 1 for use in irreversible writing using water as an ink.
3. The compound as claimed in claim 1 for use in glucose sensing application.
4. The compound as claimed in claim 1 for use in fluorescent labelling application.
5. A process for preparation of pyrene tetra boronic acid compound of formula I as claimed in claim 1 comprising steps of:
    a) adding an alkali metal periodate to a solution of a pyrene derivative in a solvent and stirring the solution for a time period ranging from 24 hours to 30 hours at a temperature ranging from 25° C. to 30° C. to obtain a reaction mixture;
    b) adding an acid into the reaction mixture of step (a) at a temperature ranging from 25° C. to 30° C. and stirring for a time period ranging from 24 hours to 30 hours to obtain pyrene tetra boronic acid of formula I.
6. The process as claimed in claim 5, wherein said pyrene derivative is (1,3,6,8-tetrakis(4,4,5,5-tetramethyl-1,3,2-dioxaborolan-2-yl)pyrene.
7. The process as claimed in claim 5, wherein said alkali metal periodate is sodium periodate.
8. The process as claimed in claim 5, wherein said acid is hydrochloric acid.
9. The process as claimed in claim 5, wherein said solvent is selected from the group consisting of tetrahydrofuran, and water or mixture thereof.

* * * * *